United States Patent [19]

Melikian-Badalian et al.

[11] Patent Number: 5,470,978
[45] Date of Patent: Nov. 28, 1995

[54] PROCESS AND INTERMEDIATES FOR THE PREPARATION OF EXCITATORY AMINO ACID RECEPTOR ANTAGONISTS

[75] Inventors: Anita Melikian-Badalian; Paul L. Ornstein, both of Indianapolis, Ind.

[73] Assignee: Eli Lilly and Company, Indianapolis, Ind.

[21] Appl. No.: 977,940

[22] Filed: Nov. 18, 1992

[51] Int. Cl.$^6$ .................. C07D 217/24; C07D 217/26; C07D 217/14; C07D 217/18

[52] U.S. Cl. ................ 546/141; 546/14; 546/142

[58] Field of Search ................ 546/14, 141, 142

[56] References Cited

U.S. PATENT DOCUMENTS 4,902,695  2/1990  Ornstein ........................ 514/307

OTHER PUBLICATIONS

Stephen R. Wilson et al., "The Cinchona Alkaloids: . . . ", *J. Org. Chem.* 1991, vol. 56, 4766–4772.
S. Wattanasin, et al., *J. Org. Chem.*, 1985, 50, 3810.
S. F. Martin, et al., *J. Org. Chem.*, 1983, 48, 5170.
T. Moriwake, *J. Org. Chem.*, 1989, 54, 4114.
Melikian–Badalian and Ornstein, LRL News, Mar. 1992, p. 31.
J. Levy, et al., *Tetrahedron Letters*, 1988, 29, 3303.
European Search Report, Feb. 7, 1994, Application No. 93309004.5.

*Primary Examiner*—C. Warren Ivy
*Assistant Examiner*—D. Margaret M. Mach
*Attorney, Agent, or Firm*—MaCharri Vorndran-Jones

[57] ABSTRACT

The present invention provides novel intermediates which are useful for the preparation of excitatory amino acid receptor antagonists. Further provided is a process to enatioselectively prepare hydroisoquinoline compounds with central nervous system activity.

12 Claims, No Drawings

PROCESS AND INTERMEDIATES FOR THE PREPARATION OF EXCITATORY AMINO ACID RECEPTOR ANTAGONISTS

BACKGROUND OF THE INVENTION

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid (EAA) receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective antagonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans- 1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connections during development and changes in the efficiency of synaptic transmission throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration make the abatement of these degenerative neurological processes an important therapeutic goal.

Excitatory amino acid excitotoxicity has been implicated in the pathophysiology of a number of acute and chronic neurodegenerative conditions, including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, perinatal hypoxia, cardiac arrest, hypoglyemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, opiate tolerance and withdrawal, anxiety, emesis, brain edema, chronic pain, convulsions, and tardive dyskinesia. The use of a neuroprotective agent, such as an NMDA receptor antagonist, is believed to be useful in treating these disorders and/or reducing the amount of neurological damage associated with these disorders. The EAA antagonists are also useful as analgesic agents.

Many EAA receptor antagonists, especially NMDA receptor antagonists, have a hydroisoquinoline base structure.

Synthesis of hydroisoquinoline and alkaloid compounds in general has traditionally been difficult. The structure of quinine was elucidated in the early 1900's, yet the first total synthesis of quinine did not appear in the literature for another thirty years. Processes that are appropriate for large-scale production of alkaloids have been particularly elusive. One known process for preparing hydroisoquinolines can enhance stereoselectivity; however, the process uses an achiral starting material and therefore, the product of the process is a racemic mixture. Wilson,S., Di Grandi J., *J. Org. Chem.* 56, 4766–4772 (1991).

SUMMARY OF THE INVENTION

This invention provides a highly enantioselective process for preparing hydroisoquinoline compounds. Suprisingly, the presently claimed enantioselective process uses non-racemic starting materials to obtain non-racemic products that are essentially enantiomerically pure. Unexpectedly, the novel C3-substituted intermediates facilitate relative and absolute stereocontrol while producing a non-racemic product using the process of the instant invention.

One group of these new intermediates are compounds of formula (I):

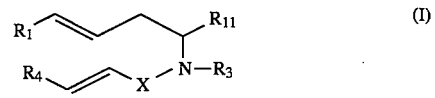

Wherein
$R_1$ is

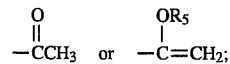

$R_{11}$ is $CO_2R_2$, $CON(R_2)_2$, $CN$, $CH_2OH$, or protected hydroxymethyl;

$R_2$ is independently hydrogen, $C_1$–$C_6$ alkyl, $C_3$–$C_6$ alkenyl, aryl, and $C_7$–$C_{16}$ arylalkyl; or the $R_2$ groups of the $CON(R_2)_2$ together with the nitrogen form a 3- to 8-member heterocyclic ring;

$R_3$ is hydrogen, $C_1$–$C_6$ alkyl, $C_3$–$C_6$ alkenyl, $CON(R_6)_2$, $SO_2R_6$, $COR_6$, benzyl, $CO_2R_6$ or substituted benzyl having from one to two substituents independently selected from the group consisting of $C_1$–$C_6$ alkyl, $C_3$–$C_8$ cycloalkyl, $NO_2$, halo, halo ($C_1$–$C_6$)alkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl; or $R_{11}$ and $R_3$ together form a 5- to 7- member heterocyclic ring;

X is —$CH_2$—,

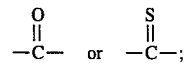

$R_4$ is hydrogen, $SO_2R_7$, $CO_2R_7$, $SiMe_3$, or $CHO$;
$R_5$ is silyl, $C_1$–$C_4$ alkyl, or $C_1$–$C_{10}$ alkanoyl; and
$R_6$, and $R_7$ independently are selected from the group consisting of $C_1$–$C_6$ alkyl, aryl, $C_7$–$C_{16}$ arylalkyl, and $C_3$–$C_6$ alkenyl;

or a pharmaceutically acceptable salt thereof.

Another group of intermediates of this invention are compounds of Formula (II)

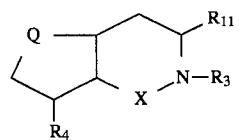

Wherein $R_{11}$, $R_2$, $R_3$, $R_4$, $R_6$, $R_7$ and X are as defined supra.

provided that, when X is —$CH_2$—, $R_{11}$ is $CO_2R_2$, and $R_4$ is hydrogen then $R_3$ is selected from the group consisting of $C_1$–$C_6$ alkyl, $C_3$–$C_6$ alkenyl, $CON(R_6)_2$, $COR_6$, $SO_2R_6$, benzyl, and substituted benzyl having from one to two substituents independently selected from the group consisting of $C_1$–$C_6$ alkyl, $C_3$–$C_8$ cycloalkyl, $NO_2$, halo, halo($C_1$–$C_6$)alkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl;

Q is

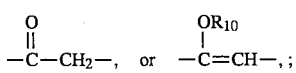

and $R_{10}$ is silyl, $C_1$–$C_4$ alkyl, or $C_1$–$C_{10}$ alkanyoyl;

or a pharmaceutically acceptable salt thereof.

The present invention further provides an enantioselective process for preparing compounds of formula (IIa)

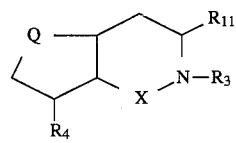

Wherein $R_{11}$, $R_2$, $R_4$, $R_6$, $R_7$, Q, $R_{10}$, and X are as defined supra.

$R_3$ is hydrogen, $C_1$–$C_6$ alkyl, $C_3$–$C_6$ alkenyl, $CON(R_6)_2$, $SO_2R_6$, $COR_6$, $CO_2R_6$, benzyl, or substituted benzyl having from one to two substituents independently selected from the group consisting of $C_1$–$C_6$ alkyl, $C_3$–$C_8$ cycloalkyl, $NO_2$, halo, halo($C_1$–$C_6$)alkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl; or $R_{11}$ and $R_3$ together form a 5- to 7- member heterocyclic ring;

or a pharmaceutically acceptable salt thereof;

which process comprises contacting a substrate of the formula (Ia)

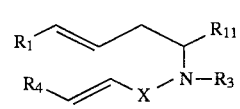

Whereran $R_1$, $R_{11}$, $R_2$, $R_3$, $R_4$, $R_5$, $R_6$, $R_7$, X, are as defined supra.;

or a pharmaceutically acceptable salt thereof;

with a silyl compound and a tertiary amine in the presence of an organic solvent.

DESCRIPTION OF THE PREFERRED EMBODIMENTS

As used herein, the term "silyl compound" refers to $Si(R_{14})_3$ Y, ($C_1$–$C_6$ alkyl)$Si(R_{14})_2$ Y, or ($C_1$–$C_6$ alkyl)$_2Si(R_{14})$ Y, wherein Y refers to halide or $OSO_2CF_3$ (triflate); and $R_{14}$ is independently selected from the group consisting of $C_1$–$C_6$ alkyl and aryl. It is intended that when the silyl compound has more than one $R_{14}$, that the $R_{14}$ groups may each independently be selected from the group consisting of $C_1$–$C_6$ alkyl and aryl.

The most preferred silyl compounds are $Si(R_{14})_3$ Y and ($C_1$–$C_6$ alkyl)$Si(R_{14})_2$ Y; wherein $R_{14}$ is selected from the group consisting of $C_1$–$C_6$ alkyl, and aryl; wherein Y is halide or triflate. Particularly preferred silyl compounds are trillares and chlorides. Host particularly preferred silyl triflates are trimethylsilyl trillate, triethylsilyl triflate, and tert-butyldimethylsilyl triflate. The term "trillate" refers to trifluoromethanesulfonate.

As used herein, the term "silyl" refers to $Si(R_{14})_3$, ($C_1$–$C_6$ alkyl)$Si(R_{14})_2$, or ($C_1$–$C_6$ alkyl)$_2Si(R_{14})$; wherein $R_{14}$ is independently selected from the group consisting of $C_1$–$C_6$ alkyl and aryl. It is intended that when the silyl has more than one $R_{14}$, that the $R_{14}$ groups may each independently be selected from the group consisting of $C_1$–$C_6$ alkyl and aryl.

The most preferred silyls are $Si(R_{14})_3$ and ($C_1$–$C_6$ alkyl)$Si)R_{14})_2$; wherein $R_{14}$ is selected from the group consisting of $C_1$–$C_6$ alkyl, and aryl. Most particularly preferred silyls are trimethylsilyl, triethylsilyl, and tert-butyldimethylsilyl.

The term "protected hydroxymethyl" refers to a substituent of the formula —$CH_2OR_{12}$; wherein $R_{12}$ refers to a hydroxy-protecting group. "Hydroxy-protecting groups" are known in the art to refer to substituents of the hydroxy group commonly employed to block or protect the hydroxy functionality while reacting other functional groups on the compound. Exemplary hydroxy-protecting groups are: $C_1$–$C_6$ alkyl, ($C_1$–$C_3$ alkyl)$OCH_3$, ($C_1$–$C_3$ alkyl)$Si(R_{13})_3$, ($C_1$–$C_3$ alkyl)$OCH_2Ph$, $CH_2O(C_1$–$C_3$ alkyl)$OCH_3$, $R_{13}C(O)$ and silyl; wherein $R_{13}$ is $C_1$–$C_6$ alkyl or aryl. Preferred hydroxy-protecting groups inlcude $C_1$–$C_3$ alkyl, ($C_1$–$C_2$ alkyl)$OCH_3$, ($C_1$–$C_2$ alkyl)$Si(R_{13})_3$, ($C_1$–$C_2$ alkyl)$OCH_2Ph$, and silyl. The most preferred hydroxy-protecting groups are silyl, $CH_2OCH_2CH_2OCH_3$, $CH_2CH_2Si(CH_3)_3$, $C_1$–$C_3$ alkyl, and $CH_2$ $OCH_2Ph$. Further examples of these groups are found in E. Haslam, "Protective Groups in Organic Chemistry", J.G.W. McOmie, Ed., Plenum Press, New York, N.Y., 1973, and T. W. Green, "Protective Groups in Organic Synthesis", John Wiley and Sons, New York, N.Y., 1981.

The term "organic solvent" includes solvents containing carbon, such as halogenated hydrocarbons, ether, toluene, xylene, benzene, and tetrahydrofuran. More preferred organic solvents include halogenated hydrocarbons and tetrahydrofuran. Especially preferred are the halogenated hydrocarbons, including halogenated hydrocarbons such as $CH_2Cl_2$, $CHCl_3$, and $ClCH_2CH_2Cl$.

"Halogenated hydrocarbons" refers to solvents of the formula $C_1$–$C_6$ alkyl-$(R_{16})_n$, $C_3$–$C_6$ alkenyl-$(R_{16})_n$, aryl-$(R_{16})_n$, $C_3$–$C_8$ cycloalkyl-$(R_{16})_n$, $C_5$–$C_8$ cycloalkenyl-$(R_{16})_n$, $C_7$–$C_{16}$ arylalkyl-$(R_{16})_n$, $C_5$–$C_8$ cycloalkyl-$(C_1$–$C_3$)alkyl-$(R_{16})_n$, $C_5$–$C_8$ cycloalkenyl-$(C_1$–$C_3$)alkyl-$(R_{16})_n$, and $C_1$–$C_{10}$ alkanoyl-$(R_{16})_n$. Wherein $R_{16}$ is independently selected from the group consisting of chloro, fluoro, and bromo. The $R_{16}$ halogens may be substituted at any available carbon atom. More preferred halogenated hydrocarbons are $C_1$–$C_6$ alkyl-$(R_{16})_n$ and $C_3$–$C_6$ alkenyl-$(R_{16})_n$. Most preferred halogenated hydrocarbons are $C_1$–$C_6$ alkyl-$(R_{16})_n$ and $C_3$–$C_6$ alkenyl-$(R_{16})_n$; wherein $R_{16}$ is chloro.

The term "tertiary amine" refers to compounds of the formula

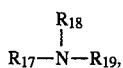

wherein $R_{17}$, $R_{18}$, and $R_{19}$ are independently selected from the group consisting of hydrogen, $C_1$–$C_8$ alkyl, $C_3$–$C_6$ alkenyl, aryl, $C_5$–$C_8$ cycloalkyl, $C_5$–$C_8$ cycloalkenyl, $C_7$–$C_{16}$ arylalkyl, $C_5$–$C_8$ cycloalkyl-($C_1$–$C_3$) alkyl, and $C_5$–$C_8$ cycloalkenyl-($C_1$–$C_3$)alkyl, or $R_{17}$ and $R_{18}$ together with the nitrogen form a five to eight member saturated heterocyclic ring which may be substituted with up to 3 $C_1$–$C_5$ alkyl substituents; or $R_{17}$ and $R_{18}$ together may form a five to eight member unsaturated heterocyclic ring with the nitrogen. Preferred tertiary amines are those wherein $R_{17}$, $R_{18}$, and $R_{19}$ are independently selected from the group consisting of hydrogen, $C_1$–$C_8$ alkyl, and $C_3$–$C_6$ alkenyl, or $R_{17}$ and $R_{18}$ together form a five to eight member saturated heterocyclic ring with the nitrogen. Examples of preferred tertiary amines include triethylamine, diisopropylethylamine, pyridine, 2,4,6-trimethylpyridine, 2,6-dimethylpryridine, 2,6-di-t-butylpyridine, 2,6-di-t-butyl-4-methylpyridine, 4-pyrrolidinopyridine, 4-dimethylaminopyridine, and N-methylmorpholine. Most preferred tertiary amines are those wherein $R_{17}$, $R_{18}$, and $R_{19}$ are $C_1$–$C_8$ alkyl.

The terms "halide", "halogen", and "halo" includes fluorine, chlorine, bromine, and iodine. The more preferred "halo" group is chlorine.

The term "halo-($C_1$–$C_6$)alkyl" refers to a halogenated alkyl substituent. The alkyl substituent may have from one to three independently selected halogens. The term includes substituents such as trichloromethyl, trifluoromethyl, dichloroethyl, 1,4-dichlorobutyl, 3-bromopentyl, 1,3-dichlorobutyl, 1,1-dichloropropyl, and the like. More preferred halo-($C_1$–$C_6$)alkyls include trichloromethyl, trichloroethyl, and trifluoromethyl. The most preferred halo-($C_1$–$C_6$)alkyl is trifluoromethyl.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

The terms "$C_1$–$C_n$ alkyl" wherein n=3–10, as used herein, represent a branched or linear alkyl group having from one to the specified number of carbon atoms. Typical $C_1$–$C_6$ alkyl groups include methyl, ethyl, n-propyl, iso-propyl, butyl, iso-butyl, sec-butyl, tert-butyl, pentyl, hexyl and the like.

The term "$C_1$–$C_{10}$ alkanoyl" represents a group of the formula C(O)($C_1$–$C_9$) alkyl. Typical $C_1$–$C_{10}$ alkanoyl groups include acetyl, propanoyl, butanoyl, and the like.

The term "$C_1$–$C_4$ alkylamino" refers to a group of the formula ($C_1$–$C_4$ alkyl)NH. The term includes either mono- or dialkylamino. The alkyl portion of the group may be straight or branched chain.

The term "$C_3$–$C_8$ cycloalkyl" represents cyclopropyl, cyclobutyl, cyclopentyl, cyclohexyl, cycloheptyl, and cyclooctyl.

The term "$C_3$–$C_8$ cycloalkyl-($C_1$–$C_3$)alkyl" represents a linear $C_1$–$C_3$ alkyl chain substituted at a terminal carbon with a $C_3$–$C_8$ cycloalkyl group. Typical alkylcycloalkyl groups include cyclohexylethyl, cyclohexylmethyl, 3-cyclopentylpropyl, and the like.

The term "$C_3$–$C_6$ alkenyl" represents an olefinically unsaturated branched or linear group having from three to six carbon atoms. The term includes such groups as 1-propenyl, 2-propenyl, iso-butenyl, hexenyl, pentenyl, and the like.

The term "$C_5$–$C_8$ cycloalkenyl" represents an olefinically unsaturated ring having five to eight carbon atoms, eg., cyclohexadienyl, cyclohexenyl, cyclopentenyl, etc.

The term "$C_5$–$C_8$ cycloalkenyl-($C_1$–$C_3$)alkyl" represents a linear $C_1$–$C_3$ alkyl group substituted with a $C_5$–$C_8$ alkenyl group.

The term "aryl" represents phenyl or condensed six-carbon rings of other aromatic derivatives. For example, an aryl group may be phenyl or naphthyl. The term "aryl" includes but is not limited to an aryl substituted with one to two substituents independently selected form the group consisting of $C_1$–$C_6$ alkyl, $C_3$–$C_8$ cycloalkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl. The aryl substituents may be located at any available position on the aryl ring.

The term "$C_7$–$C_{16}$ arylalkyl" represents an aryl-($C_1$–$C_{10}$)alkyl substituent wherein the alkyl group is linear, such as benzyl, phenethyl, and 3-phenylpropyl; or branched.

The term "heterocyclic ring" refers to an unsubstituted or substituted 5- to 7-membered monocyclic heterocyclic ring which may be saturated or unsaturated. The heterocyclic ring consists of carbon atoms and from one to three heteroatoms independently selected from the group consisting of nitrogen, oxygen, and sulfur. The nitrogen and sulfur heteroatoms may optionally be oxidized, and the nitrogen heteroatoms may optionally be quaternized. The heterocyclic ring is unsubstituted or substituted with 1, 2, or 3 substituents independently selected from the group consisting of halo, halo($C_1$–$C_4$)alkyl, $C_1$–$C_4$ alkyl, $C_1$–$C_{10}$ alkanoyl, and $C_1$–$C_4$ alkylamino. More preferably the heterocyclic ring is saturated and substituted. The most preferred substitution is $C_1$–$C_4$ alkyl.

The most preferred heterocyclic ring formed by $R_{11}$ and $R_3$ when X is C(O) or C(S) is an oxazolidin-5-one ring.

The term "benzyl" refers to a group of the formula $CH_2Ph$. The term "substituted benzyl" refers to a benzyl group which may be substituted with one to two independently selected substituents at any desired position on the benzyl ring. The substituents are selected from the group consisting of from the group consisting of $C_1$–$C_6$ alkyl, $C_3$–$C_8$ cycloalkyl, $NO_2$, halo, halo($C_1$–$C_6$)alkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl.

Abbreviations used herein have their accepted meaning, unless stated otherwise. For example, "Me" refers to methyl, "Et" refers to ethyl, "Bu" refers to butyl, "t-Bu" and "t-butyl" refers to tertiary butyl, and "Ph" refers to phenyl.

The term

refers to a carbonyl substituent. Likewise, the term

refers to a thiocarbonyl. substituent.

Certain compounds of this invention can form acid addition salts with a wide variety of inorganic and organic acids. Typical acids which can be used include sulfuric, hydrochloric, hydrobromic, phosphoric, 30 hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the Formula (I) and Formula (II) are especially preferred.

This invention provides novel intermediate compounds of Formula (I) and Formula (II). The Formula (I) and Formula (II) compounds are useful in the preparation of hydroiso- quinoline compounds that are useful agents affecting the central nervous system. Table I illustrates several of the Formula (I) intermediates. The terms in the column headings of Table I refer to Formula (I). The abbreviation "PHM" refers to protected hydroxymethyl as defined herein above.

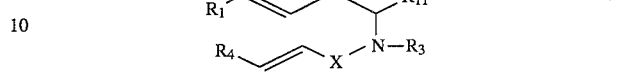

TABLE I

| $R_1$ | $R_2$ | $R_3$ | X | $R_4$ | $R_5$ | $R_6$ | $R_7$ | $R_{11}$ |
|---|---|---|---|---|---|---|---|---|
| $CH_3C=O$ | $CH_3$ | $CH_2Ph$ | $C=O$ | CHO | — | — | — | $CO_2R_2$ |
| $CH_3C=O$ | $C_2H_5$ | $CH_2Ph$ | $C=O$ | H | — | — | — | $CON(R_2)_2$ |
| $CH_3C=O$ | $C_3H_7$ | $CH_2Ph$ | $C=O$ | $CO_2R_7$ | — | — | $CH_3$ | $CO_2R_2$ |
| $CH_3C=O$ | $C_3H_7$ | $CH_2Ph$ | $C=O$ | $SO_2R_7$ | — | — | $PhCH_3$ | $CON(R_2)_2$ |
| $CH_3C=O$ | — | $CH_2Ph$ | $C=O$ | CHO | — | — | — | CN |
| $CH_3C=O$ | $C_8H_9$ | $CH_2Ph$ | $C=O$ | H | — | — | — | $CO_2R_2$ |
| $CH_3C=O$ | — | $CH_2Ph$ | $C=O$ | $CO_2R_7$ | — | — | $C_2H_5$ | $CH_2OH$ |
| $CH_3C=O$ | — | $CH_2Ph$ | $C=O$ | $SO_2R_7$ | — | — | $PhCH_3$ | PHM |
| $CH_3C=O$ | — | $CH_2Ph$ | $C=O$ | CHO | — | — | — | CN |
| $CH_3C=O$ | — | $CH_2Ph$ | $C=O$ | H | — | — | — | PHM |
| $CH_3C=O$ | $C_4H_9$ | $CH_2Ph$ | $C=O$ | $CO_2R_7$ | — | — | $C_3H_7$ | $CO_2R_2$ |
| $(OR_5)C=CH_2$ | — | $CH_3$ | $C=S$ | CHO | $CH_3$ | — | — | CN |
| $(OR_5)C=CH_2$ | — | $C_3H_8$ | $C=S$ | H | $C_2H_5$ | — | — | PHM |
| $(OR_5)C=CH_2$ | — | $CH_3$ | $C=S$ | $CO_2R_7$ | $C_3H_7$ | — | $CH_3$ | $CH_2OH$ |
| $(OR_5)C=CH_2$ | $C_2H_5$ | $SO_2R_6$ | $C=S$ | $SO_2R_7$ | $C_6H_5$ | —$CH_3$ | $C_3H_7$ | $CO_2R_2$ |
| $(OR_5)C=CH_2$ | $C_3H_7$ | $CH_2Ph$ | $C=S$ | CHO | silyl | — | — | $CON(R_2)_2$ |
| $(OR_5)C=CH_2$ | $PhC_2H_4$ | $C_3H_5$ | $C=S$ | $CO_2R_7$ | $CH_3$ | — | $PhCH_2$ | $CO_2R_2$ |
| $(OR_5)C=CH_2$ | — | $CH_3$ | $C=S$ | $SO_2R_7$ | $C_2H_5$ | — | $CH_3$ | CN |
| $(OR_5)C=CH_2$ | $C_6H_5$ | $SO_2R_6$ | $C=S$ | CHO | $C_3H_7$ | $C_2H_5$ | — | $CON(R_2)_2$ |
| $(OR_5)C=CH_2$ | — | $CH_2Ph$ | $C=S$ | H | $C(O)CH_3$ | — | — | PHM |
| $(OR_5)C=CH_2$ | — | $CH_3$ | $C=S$ | $CO_2R_7$ | silyl | — | $C_2H_5$ | CN |
| $(OR_5)C=CH_2$ | $PhCH_2$ | $C_3H_5$ | $C=S$ | $SO_2R_7$ | silyl | — | $C_3H_7$ | $CO_2R_2$ |
| $(OR_5)C=CH_2$ | $CH_3$ | $CH_3$ | $C=S$ | CHO | $CH_3$ | — | — | $CON(R_2)_2$ |
| $(OR_5)C=CH_2$ | — | $SO_2R_6$ | $C=O$ | H | $C_2H_5$ | $C_2H_5$ | — | CN |
| $(OR_5)C=CH_2$ | — | $CH_2Ph$ | $C=O$ | $CO_2R_7$ | $C_3H_7$ | — | $PhCH_2$ | PHM |
| $(OR_5)C=CH_2$ | $C_3H_7$ | $CH_3$ | $C=O$ | $SO_2R_7$ | $C(O)CH_3$ | — | $PhCH_2$ | $CO_2N(R_2)_2$ |
| $(OR_5)C=CH_2$ | — | $C_3H_5$ | $C=O$ | $SiMe_3$ | silyl | — | — | CN |
| $CH_3C=O$ | — | $CH_3$ | $C=S$ | H | — | — | — | PHM |
| $CH_3C=O$ | — | $SO_2R_6$ | $C=S$ | $CO_2R_7$ | — | $CH_3$ | $C_3H_7$ | PHM |
| $CH_3C=O$ | — | $CH_3$ | $C=S$ | $SO_2R_7$ | — | — | $C_3H_7$ | CN |
| $(OR_5)C=CH_2$ | $PhC_2H_5$ | $CH_2Ph$ | $C=O$ | CHO | silyl | — | — | $CO_2R_2$ |
| $(OR_5)C=CH_2$ | — | $COR_6$ | $S=O$ | H | $C(O)C_2H_5$ | $C_3H_7$ | — | CN |
| $(OR_5)C=CH_2$ | $CH_2=C_3H_6$ | $CON(R_6)_2$ | $CH_2$ | $SiMe_3$ | silyl | $CH_2Ph$ | — | $CON(R_2)_2$ |
| $(OR_5)C=CH_2$ | $CH_3$ | $C_2H_5$ | $CH_2$ | $SO_2R_7$ | silyl | — | $C_3H_7$ | $CO_2R_2$ |
| $(OR_5)C=CH_2$ | — | $COR_6$ | $CH_2$ | $SiMe_3$ | silyl | $CH_2Ph$ | — | PHM |
| $(OR_5)C=CH_2$ | — | $SO_2R_6$ | $CH_2$ | H | $CH_3$ | $CH_3$ | — | CN |
| $(OR_5)C=CH_2$ | $CH_2=C_2H_4$ | $CH_2Ph$ | $CH_2$ | $CO_2R_7$ | $C_2H_5$ | — | $C_2H_5$ | $CON(R_2)_2$ |
| $CH_3C=O$ | — | $CH_2PhCH_3$ | $CH_2$ | $SO_2R_7$ | — | — | $CH_3$ | PHM |
| $CH_3C=O$ | — | $CH_2PhC_2H_5$ | $CH_2$ | CHO | — | — | — | CN |
| $CH_3C=O$ | — | $COR_6$ | $CH_2$ | $SiMe_3$ | — | — | $C_3H_7$ | PHM |
| $CH_3C=O$ | $C_2H_5$ | $CON(R_6)_2$ | $CH_2$ | $CO_2R_7$ | — | $C_2H_5$ | $PhCH_2$ | $CO_2R_2$ |
| $CH_3C=O$ | — | $CH_3$ | $CH_2$ | $SO_2R_7$ | — | — | $C_6H_5$ | CN |

Table II illustrates other new intermediates of this invention. The terms in the colum headings of Table II refer to formula (II). The abbreviation "PHM" refers to protected hydroxymethyl as defined herein above.

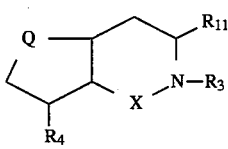
(II)

The formula (II) asymmetric centers are the substituted carbon atom adjacent to the ring $NR_3$ (3), the two bridgehead carbon atoms (4a and 8a) and the substituted carbon atom at (8) when $R_4$ is not hydrogen. The asymmetric centers of formula (II) are indicated by the carbon number above. As such, the compounds can exist as diastereomers, each of which can exist as a racemic mixture of enantiomers.

TABLE II

| Q | $R_2$ | $R_3$ | X | $R_4$ | $R_6$ | $R_{10}$ | $R_{11}$ |
|---|---|---|---|---|---|---|---|
| $CH_2C=O$ | $CH_3$ | $CH_2Ph$ | C=O | CHO | — | — | $CO_2R_2$ |
| $CH_2C=O$ | $C_2H_5$ | $CH_2Ph$ | C=O | H | — | — | $CON(R_2)_2$ |
| $CH_2C=O$ | $C_3H_7$ | $CH_2Ph$ | C=O | $CO_2R_7$ | — | — | $CO_2R_2$ |
| $CH_2C=O$ | $C_3H_5$ | $CH_2Ph$ | C=O | $SO_2R_7$ | — | — | $CON(R_2)_2$ |
| $CH_2C=O$ | — | $CH_2Ph$ | C=O | CHO | — | — | CN |
| $CH_2C=O$ | $C_8H_9$ | $CH_2Ph$ | C=O | H | — | — | $CO_2R_2$ |
| $CH_2C=O$ | — | $CH_2Ph$ | C=O | $CO_2R_7$ | — | — | PHM |
| $CH_2C=O$ | — | $CH_2Ph$ | C=O | $SO_2R_7$ | — | — | CN |
| $CH_2C=O$ | — | $CH_2Ph$ | C=O | CHO | — | — | PHM |
| $CH_2C=O$ | $C_6H_{11}$ | $CH_2Ph$ | C=O | H | — | — | $CO_2R_2$ |
| $CH_2C=O$ | — | $CH_2Ph$ | C=O | $CO_2R_7$ | — | — | CN |
| $(OR_{10})C=CH_2$ | — | $CH_3$ | C=S | CHO | — | $CH_3$ | PHM |
| $(OR_{10})C=CH_2$ | — | $CH_2H_3$ | C=S | H | — | $C_2H_5$ | $CH_2OH$ |
| $(OR_{10})C=CH_2$ | $CH_3$ | $CON(R_6)_2$ | C=S | $CO_2R_7$ | $CH_3$ | silyl | $CO_2R_2$ |
| $(OR_{10})C=CH_2$ | $C_2H_5$ | $SO_2R_6$ | C=S | $SO_2R_7$ | $CH_3$ | $C(O)CH_3$ | $CON(R_2)_2$ |
| $(OR_{10})C=CH_2$ | H | $CH_2Ph$ | C=S | CHO | — | $C(O)CH_3$ | $CO_2R_2$ |
| $(OR_{10})C=CH_2$ | — | $CH_3$ | C=S | CHO | — | silyl | $CH_2OH$ |
| $(OR_{10})C=CH_2$ | H | $C_3H_5$ | C=S | H | — | $CH_3$ | $CO_2R_2$ |
| $(OR_{10})C=CH_2$ | $C_8H_9$ | $CON(R_6)_2$ | C=S | $CO_2R_7$ | $CH_3$ | $C_2H_5$ | $CON(R_2)_2$ |
| $(OR_{10})C=CH_2$ | $C_6H_5$ | $SO_2R_6$ | C=S | $SO_2R_7$ | $C_2H_5$ | $C_3H_7$ | $CO_2R_2$ |
| $(OR_{10})C=CH_2$ | — | $CH_2Ph$ | C=S | CHO | — | silyl | CN |
| $(OR_{10})C=CH_2$ | $C_6H_9$ | $CH_3$ | C=S | H | — | $C(O)CH_3$ | $CON(R_2)_2$ |
| $(OR_{10})C=CH_2$ | H | $C_2H_5$ | C=S | $CO_2R_7$ | — | silyl | $CO_2R_2$ |
| $(OR_{10})C=CH_2$ | — | $CON(R_6)_2$ | C=S | $SO_2R_7$ | $CH_3$ | $CH_3$ | PHM |
| $(OR_{10})C=CH_2$ | — | $SO_2R_6$ | C=O | CHO | $C_2H_5$ | $C_2H_5$ | CN |
| $(OR_{10})C=CH_2$ | $C_7H_7$ | $CH_2Ph$ | C=O | H | — | silyl | $CO_2R_2$ |
| $(OR_{10})C=CH_2$ | — | $CH_3$ | C=O | $CO_2R_7$ | — | $C(O)CH_3$ | PHM |
| $(OR_{10})C=CH_2$ | — | $C_2H_5$ | C=O | CHO | — | $C(O)CH_3$ | PHM |
| $CH_2C=O$ | $CH_3$ | $CON(R_6)_2$ | C=S | H | $C_6H_5$ | — | $CO_2R_2$ |
| $CH_2C=O$ | — | $SO_2R_6$ | C=S | $CO_2R_7$ | $CH_3$ | — | PHM |
| $CH_2C=O$ | — | $CH_3$ | C=S | $SO_2R_7$ | — | — | CN |
| $(OR_{10})C=CH$ | $CH_3$ | $CH_2Ph$ | C=O | CHO | — | silyl | $CO_2R_2$ |
| $(OR_{10})C=CH$ | — | $COR_6$ | C=S | H | $C_3H_7$ | silyl | $CH_2OH$ |
| $(OR_{10})C=CH$ | $C_6H_5$ | $CON(R_6)_2$ | $CH_2$ | $SiMe_3$ | $CH_2Ph$ | silyl | $CON(R_2)_2$ |
| $(OR_{10})C=CH$ | $C_6H_{11}$ | $COR_6$ | $CH_2$ | $SO_2R_7$ | $CH_3$ | silyl | $CO_2R_2$ |
| $(OR_{10})C=CH$ | — | $C_2H_5$ | $CH_2$ | $SiMe_3$ | — | $CH_3$ | PHM |
| $(OR_{10})C=CH$ | — | $SO_2R_6$ | $CH_2$ | H | $C_2H_5$ | $C_2H_5$ | CN |
| $CH_2C=O$ | — | $CH_2PhCH_3$ | $CH_2$ | $CO_2R_7$ | — | — | PHM |
| $CH_2C=O$ | — | $CON(R_6)_2$ | $CH_2$ | $SO_2R_7$ | $C_2H_5$ | — | CN |
| $CH_2C=O$ | $PhC_2H_4$ | $CH_2Ph$ | $CH_2$ | CHO | — | — | $CO_2R_2$ |
| $(OR_{10})C=CH$ | — | $COR_6$ | C=O | $SiMe_3$ | $CH_2Ph$ | $C(O)C_2H_5$ | PHM |
| $(OR_{10})C=CH$ | — | $COR_6$ | $CH_2$ | $CO_2R_7$ | $CH_3$ | $C(O)C_3H_7$ | CN |
| $(OR_{10})C=CH$ | — | $CON(R_6)_2$ | $CH_2$ | $SO_2Ph$ | $CH_2Ph$ | silyl | PHM |

The formula (I) compounds of the present invention possess at least one asymmetric center. Additionally, the formula (II) compounds of the present invention possess at least three asymmetric carbon atoms as shown below:

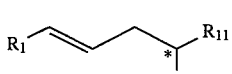
(I)

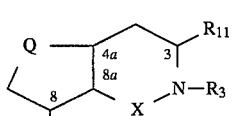
(IIa)

The stereochemistry of the double bonds to which $R_1$ and $R_4$ are attached when $R_4$ is not hydrogen may each be pure E, pure Z, or the EZ mixture.

The present invention encompasses not only the racemates, but also the respective enantiomers.

The more preferred relative and absolute stereochemistry is shown in the formulas (I') and (II') below.

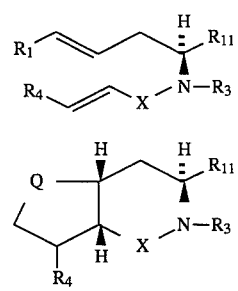

It will be understood that all eight isomers encompassed by the present invention can be prepared as described in the following paragraphs depending on the choice of reactants.

The novel intermediates of Formula (I) may be prepared by a variety of chemical methods known to the organic chemist. Likewise, intermediates of Formula (Ia) can be prepared by methods known to the artisan.

This invention provides a highly enantioselective process for the preparation of compounds of Formula (II) and Formula (IIa). This process is especially advantageous because it is appropriate for large scale equipment. The process may also be appropriate for adaptation to polymer supported reagents. The equipment necessary to carry out the process is of the type commonly found in organic chemical processing plants.

The concentration of the reactants is not critical. The art worker can alter the concentration of the reactants to achieve the desired rate of reaction and product yield.

The length of time for carrying out the processes described are not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

The preparation of the novel compounds (6) or (7) starting material for the novel process of this invention is illustrated in Scheme I. All of the other reagents used in the novel process are well known to the organic chemist, and can easily be purchased or prepared by established chemical methods. For the convenience of the organic chemist, the preparation of the intermediate starting materials is generally described in the following paragraphs.

The corresponding novel thiocarbonyl intermediate may be prepared by standard techniques using Lawesson's Reagent. Informative references describing the use of Lawesson's Reagent for the thiation of amides include *Synthesis* 941 (1979) and *Tetrahedron* 35, 2433 (1979), which are hereby incorporated by reference in their entireties. Preparation of the thiocarbonyl intermediate is generally described in Scheme I. All other starting materials used in the process are well known to the organic chemist and can easily be purchased or prepared.

The meaning of the terms and abbreviations used in Scheme I are as described herein above. The term "$R_3HAL$" refers to a halogen-substituted $R_3$ compound; wherein $R_3$ is defined above and "HAL" is a halide. The term "$R_3HAL$" includes, but is not limited to compounds such as 4-MeO-Ph-CH$_2$Br (4-methoxybenzylbromide), 3,4-diMeO- Ph-CH$_2$Br (3,4-dimethoxybenzyl bromide), CH$_3$Br, CH$_3$Cl, CH$_3$I, CH$_2$=CHCH$_2$Br, CH$_2$=CHCH$_2$Cl, CH$_2$=CHCH$_2$I, PhCH$_2$Br, PhCH$_2$Cl, PhCH$_2$I, and the like.

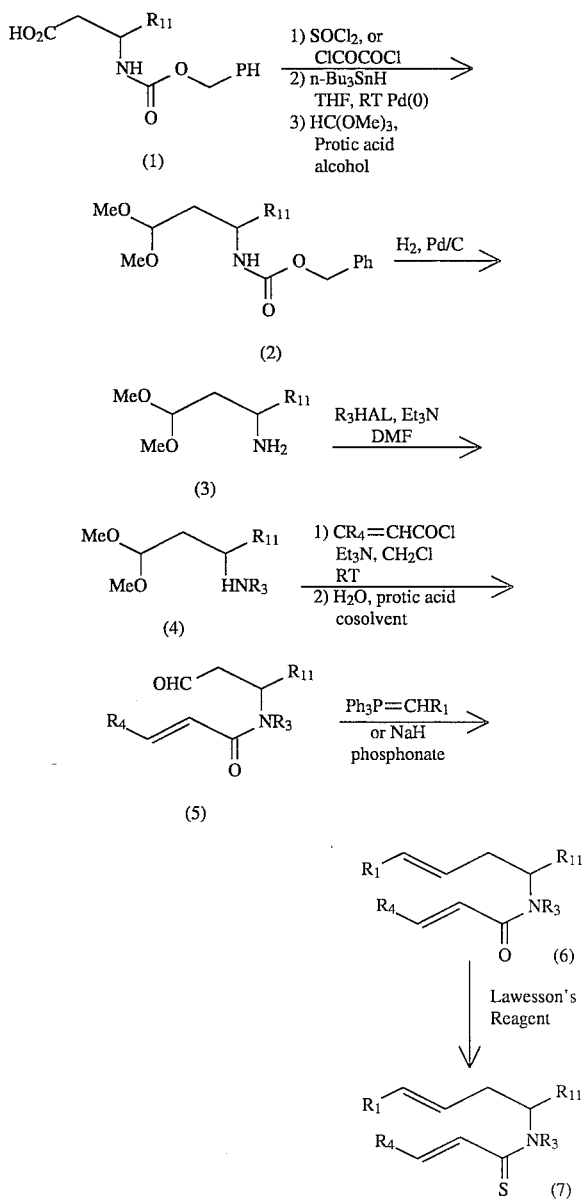

SCHEME I
ENANTIOSELECTIVE INTRAMOLECULAR DIELS-ALDER
APPROACH TO HYDROISOQUINOLINONES

The Formula (1) starting material can be purchased from recognized vendors of chemical reagents. Formula (1) is contacted with thionyl chloride or oxalyl chloride under an inert atmosphere. Later, tetrahydrofuran and tributyltinhydride are added. More preferably, a catalyst such as a palladium (0) reagent is added to the mixture. Most preferably the palladium reagent is tetrakis(triphenylphosphine) palladium (0). Additional tributyltinhydride may be added as needed. The resulting Formula (1) intermediate may be washed and purified if desired.

The Formula (1) intermediate is contacted with an alcohol, trimethyl orthoformate, and a strong protic acid. Preferably the alcohol is $C_1$–$C_6$ alcohol. Most preferably the alcohol is methanol. Strong protic acids such as hydrochloric acid, p-toluenesulfonic acid, and camphorsulfonic acid are appropriate. The most preferred strong protic acid is p-toluenesulfonic acid. Most preferably, the reaction mixture is refluxed and cooled before using the acetal (2) in the catalytic hydrogenation step.

The catalytic hydrogenation step is completed by contacting a portion of the acetal (2) prepared above with an appropriate solvent and a catalyst in the prescence of hydrogen. The solvent must be carefully selected to avoid transesterification when $R_{11}$ is an ester. When $R_{11}$ is an ester preferable solvents include methanol and ethyl acetate. The most preferable solvent is methanol. A preferred catalyst is 5% palladium on carbon. The mixture may be agitated under pressure. The product (3) may be isolated as an oil.

Alternatively, the product (3) may be prepared by catalytic transfer hydrogenation using a catalyst such as 10% Pd/C in the presence of a protic solvent and an appropriate hydrogen source. A preferred protic solvent is methanol. Preferred hydrogen sources include ammonium formate, triethylammonium formate, tetrabutylammonium formate, cyclohexene, and 1,3-cyclohexadieneo Most preferred hydrogen sources include ammonium formate, and 1,3-cyclohexadiene.

A portion of tertiary amine base, an aprotic solvent, and an appropriate halide is added to the product (3) of the hydrogenation step. Preferred tertiary amine bases include triethylamine, diisopropylethylamine, and N-methylmorpholine. The most preferred tertiary amine base is triethylamine. The most preferred aprotic solvent is dimethylformamide. Preferred halides include alkenyl halide, arylalkyl halide, and alkyl halide. For example, when methyl 3S,4aS, 8aR-N-benzyl-1,6-dioxo- 1,2,3,4,4a,5,6,7,8,8a-decahydroisoquinoline-3-carboxylate is desired, benzyl bromide is the most preferred halide. The mixture may be agitated at about room temperature. The product (4) may be isolated and characterized by nuclear magnetic resonance spectroscopy before using it in subsequent reactions.

The product (4) of the alkylation reaction is contacted with dichloromethane, triethylamine, and an appropriate acylating agent. The acylating agent should be selected to correspond to the desired $R_4$ substituent. Appropriate acylating agents may be prepared from the following acids fumaric acid monoethyl ester (Aldrich), fumaraldhydic acid (*Chem. Abst.* 66 28364h (1967)), and 3-benzenesulfonylacrylic acid (*Chem. Abst.* 71 112555g (1969)). The carboxylic acid may be converted to the corresponding acylating agent by known methods. Campbell, P. G., *J. Org. Chem.* 26 697 (1961). Other useful acylating agents include 3-(trimethylsilyl)-2-propenoyl chloride (Wilson,S., Di Grandi J., *J. Org. Chem.* 56, 4766–4772 (1991)), and acroylyl chloride (Aldrich). The most preferred acylating agent is acryloyl chloride.

The mixture may be agitated and may be extracted with dichloromethane when the reaction has reached the desired percent completion. For hydrolysis of the acetal to the corresponding aidehyde, intermediate (5) is mixed with an aqueous acid and a cosolvent. Preferred cosolvents include methanol, acetonitrile, and tetrahydrofuran. Preferred acids include hydrochloric and sulfonic acid. More preferably $CH_3CN$ is added with a water and an acid such as hydrochloric acid or a sulfonic acid. Most preferably, the acid is hydrochloric acid. The mixture may be agitated to speed the production of intermediate (5).

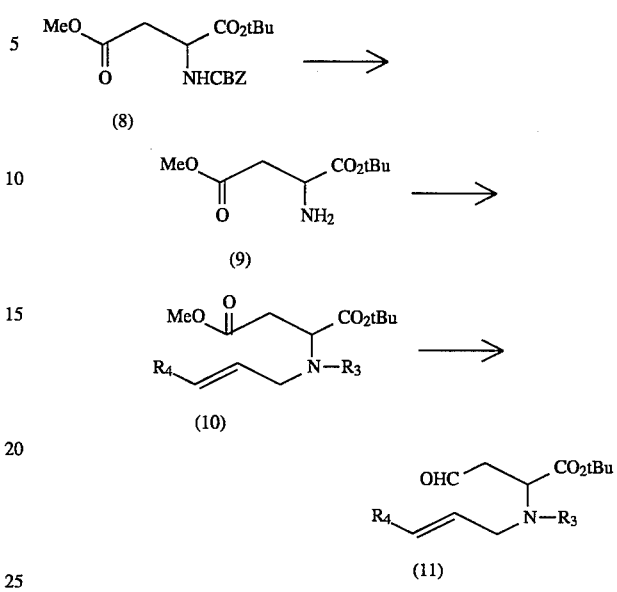

The hydrolysis described above is not effective for compounds in which X is $CH_2$ and $R_3$ is hydrogen, alkyl, alkenyl, benzyl, or substituted benzyl. Thus, when these compounds such as compound (11) are desired, the reaction illustrated in Scheme (II) may be utilized. The hydrogenolysis of compound (8) to compound (9) may be completed as described herein. The alkylation of compound (9) to form the methyl ester (10) may be completed using the methods described above. The preparation of the starting material (8) is known. Gregory, H., et al. *J. Chem. Soc.* 1968, 715. The reduction of the methyl ester (10) to form the corresponding aldehyde (11) may be completed by the method described in Gunter et al. *Liebigs Ann. Chem.* 1984, 1424. The resulting compounds (11) may be used as intermediate (5) in subsequent reactions.

The intermediate (5) is contacted with a Wittig or Horner-Emmons reagent. A most preferred Wittig reagent is (triphenylphosphoranylidene) acetone. Alternatively, the intermediate may be contacted with 1-(diethylphosphono)-2-propanone or 1-(diisopropylphosphono)-2-propanone and a base in tetrahydrofuran.

Preferred bases include NaH, KOt-Bu, $KN(SiMe_3)_2$, $NaN(SiMe_3)_2$, and $LiN(SiMe_3)_2$. Horner-Emmons reagents are preferred to facilitate purification of the desired product. The mixture is subjected to a temperature of from about 0° C. to about reflux under an inert atmosphere. The desired compound (6) may be isolated and characterized.

When the corresponding thiocarbonyl (7) is desired, the compound (6) may be contacted with Lawesson's Reagent as represented in Scheme I.

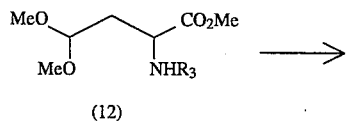

-continued
SCHEME II

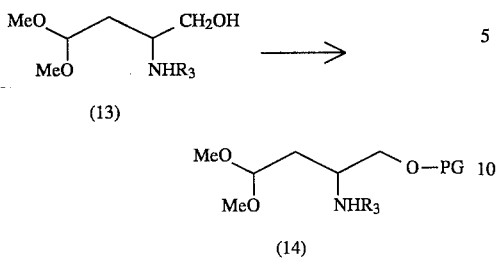

Alternatively, the process of Scheme (III) may be used to prepare other useful starting materials. As used in Scheme (III) "PG" is $R_2$ or $R_{12}$, "CBZ" represents carbobenzoxy and "HAL" represents halide.

The process of Scheme (III) may be used when a protected hydroxymethyl group is desired at the $R_{11}$ position. As shown in Scheme (III), the compounds of formula (12) are reduced using lithium borohydride and tetrahydrofuran to prepare compounds of formula (13). Alternatively, (13) may be prepared by the hydrolysis of the ester (12) to form the carboxylic acid intermediate, followed by reduction to (13). The hydrolysis of the ester (12) may be completed using a base, water, and a cosolvent. Desirable bases include sodium hydroxide, lithium hydroxide, and potassium hydroxide. The most preferred cosolvent is methanol. The carboxylic acid intermediate is then reduced using borane dimethylsulfide in tetrahydrofuran to form compounds of formula (13).

The (14) compounds are prepared by contacting (13) with a compound of the formula PG-HAL and tetrahydrofuran. Alternatively, PG-HAL may be added with dichloromethane, a base, and a tertiary amine. The terms "base" and "tertiary amine" are as defined supra.

The skilled artisan will recognize that compounds of formula (14) can be alkylated by general chemical methods. This process provides compounds wherein $R_{11}$ is a protected hydroxymethyl and X is $CH_2$.

SCHEME IV

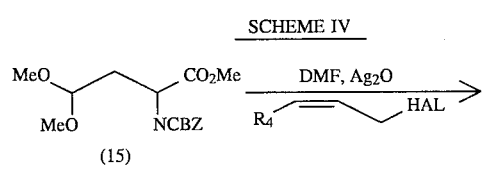

-continued
SCHEME IV

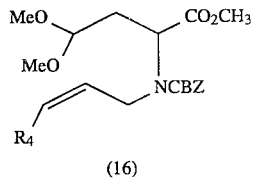

When $R_3$ is carbamate or amide, the alkylation may be completed by using an allylhalide, silver oxide, and dimethylformamide to accomplish the alkylation. *J.Med. Chem.*, 29, 802–809 (1986). This reaction is illustrated in Scheme (IV). Preferred allyl halides are allylbromide and allyliodide.

When compounds wherein $R_4$ is $SO_2Ph$ are desired and $R_3$ is carbamate, amide, alkyl, alkenyl, benzyl, or substituted benzyl, the alkylation can be run using 3-bromo-1-(phenyl sulfonyl)-1-propene. The 3-bromo-1-(phenyl sulfonyl)-1-propene can be prepared using 1-propenylphenylsulfonate, bromine, and triethylamine. This reaction is described in greater detail in *J. Org. Chem.*, 44, 18, 3278 (1979). Other preferred allyl bromides are 4-bromocrotonate, which is commercially available, and 4-bromocrotonaldehyde, which may be prepared by known methods. (*Chem. Abst.* 91 56319g (1979) and *Chem. Abst.* 74 25 140837f (1971)).

SCHEME V

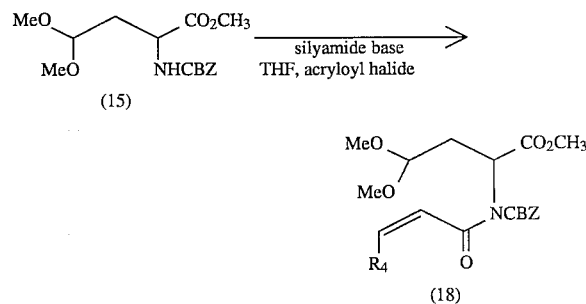

When $R_3$ is carbamate or amide, the acylation may be completed using a silylamide base, acryloyl halide, and an aprotic solvent. The preferred silylamides are $KN(SiMe_3)_2$, $NaN(SiMe_3)_2$, and $LiN(SiMe_3)_2$. The preferred acryloyl halide is acryloyl chloride. The most preferred aprotic solvent is tetrahydrofuran. The reaction is illustrated in Scheme (V).

Scheme VI

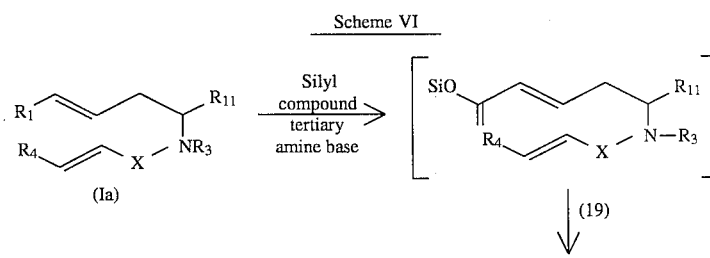

-continued
Scheme VI

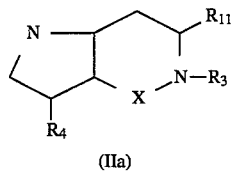

(IIa)

The novel process of this invention is represented by Scheme (VI). The starting material for the new Diels Alder-type process is an appropriate Formula (Ia) compound which may be prepared by the previously described method. A portion of the Formula (Ia) compound is contacted with an appropriate silyl compound, a portion of a tertiary amine and an appropriate solvent. Appropriate silyl compounds include silyl triflates and silyl chlorides. Preferred silyl compounds are trimethylsilyl triflate, triethylsilyl triflate, and t-butyldimethylsilyl trillate. The most preferred silyl compound is triethylsilyl triflate. Preferred teriary amines include diisopropylethylamine, pyridine, 4-N,N-dimethylaminopyridine (DMAP) and triethylamine. The most preferred tertiary amine is triethylamine. Appropriate solvents include halogenated hydrocarbons, ether, toluene, xylene, benzene, and tetrahydrofuran. The more preferred solvents include halogenated hydrocarbons such as $CH_2Cl_2$, $CHCl_3$, and $ClCH_2CH_2Cl$, and tetrahydrofuran. The most preferred solvent is dichloromethane.

The terms and abbreviations used in Scheme (VI) are as hereinbefore described.

The process is effective over a broad temperature range. The process is preferrably carried out at from about $-78°$ C. to about $80°$ C. The process may be carried out with a Lewis acid present. Preferable Lewis acids include diethylaluminum chloride, ethylaluminum dichloride, tin (IV) chloride, boron trifluoride diethyl etherate, silica gel, and titanium(IV) chloride. The process is also effective when a Lewis acid is not present.

When the Diels Alder-type process has gone to the desired degree of completion, the product (IIa) is isolated from the reaction medium. When the Q group is

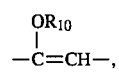

the enol ether may be hydrolized by standard methods. The artisan can readily recognize appropriate hydrolizing agents, for example aqueous acid and a cosolvent or potassium fluoride in methanol. Preferred cosolvents include methanol, acetonitrile, and tetrahydrofuran. Preferred acids include hydrochloric and sulfonic acid. The residue may be partitioned between water and an appropriate organic solvent. A preferred organic solvent is ethyl acetate. The organic extracts may be washed with brine and contacted with an appropriate drying agent. A preferred drying agent is magnesium sulfate. The product may then be isolated using flash chromatography, distillation, high performance liquid chromatography, or other appropriate methods. The product may be recrystallized and isolated.

A number of expedients may be utilized for the isolation. For example, the product may be isolated by simple filtration methods. Such filtration methods include filtration by sand, sintered glass, porous membrane, or paper. Alternatively, the product may be recovered by centrifugation. The most preferred isolation method is simple filtration using porous membrane, sintered glass, or paper.

No further purification of the product is necessary. The novel intermediate product is used in the preparation of important excitatory amino acid receptor antagonists.

The conversion of the intermediate product to the desired isoquinolinecarboxylic acid is accomplished by methods well known to the skilled chemist. Some of the possible products of the conversion include (3S,4aR,6S,8aR)-6-(phosphonomethyl)-1,2,3,4,4a,5,6,7,8,8 a-decahydroisoquinoline-3-carboxylic acid, (3S,4aR,6S,8aR)-6 -(( 1H-tetrazol-5-yl)methyl)-1,2,3,4,4a,5,6,7,8,8 a-decahydroisoquinoline-3-carboxylic acid, and (3S,4aR, 6S,8aR)-6-(carboxymethyl)-1,2,3,4,4a,5,6,7,8,8 a-decahydroisoquinoline-3-carboxylic acid.

For the convenience of the skilled chemist, the simple conversion of the intermediate product (IIa) to the corresponding excitatory amino acid receptor antagonist is represented in Scheme (VII). If the Q substitutent was $$\begin{array}{c} OR_{10} \\ | \\ -C=CH- , \end{array}$$

then the enol ether should be hydrolized prior to the reaction of Scheme (VII). The terms used in Scheme (VII) are as described herein above and the additional terms have the following meanings:

$R_{20}$ is $PO_3Et_2$, CN, or $CO_2Et$.

$R_{21}$ is $PO_3H_2$, tetrazole, or $CO_2H$. The term "tetrazole" includes:

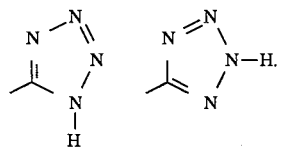

SCHEME VII

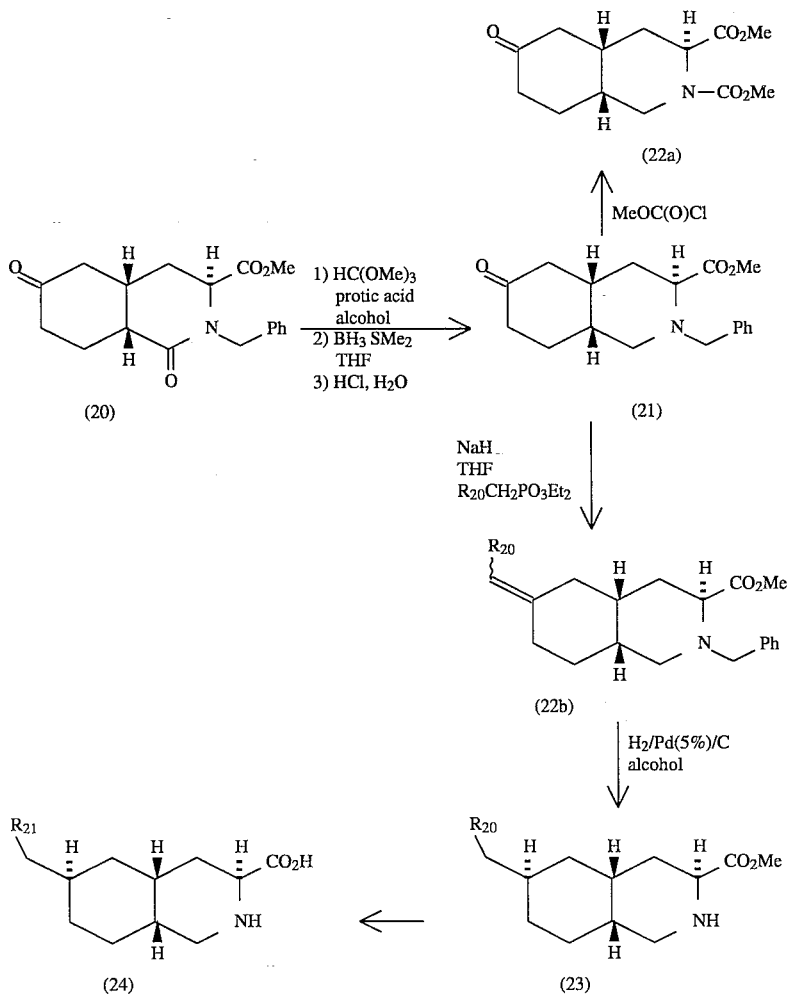

As shown in Scheme (VII), a compound of formula (20) is reduced by first contacting (20) with trimethyl orthoformate, a protic acid, and an alcohol. Next, $BH_3 \cdot SMe_2$ in tetrahydrofuran, then hydrochloric acid with water is added to the mixture to produce a compound of formula (21). The (21) compound may be contacted with MeOC(O)Cl to produce the (22a) compound.

Alternatively, (21) may be contacted with sodium hydride, tetrahydrofuran, and $R_{20}CH_2PO_3Et_2$ to produce compounds of formula (22b). The (22b) compound is subject to catalytic hydrogenation. The catalytic hydrogenation is completed using a catalyst such as palladium on carbon in the presence of hydrogen and a cosolvent. Preferred cosolvents include methanol and ethanol. The conversion from (22b) to (23) may optionally be completed in the presence of acetic acid.

The (23) compounds wherein $R_{20}$ is $PO_3Et_2$ or $CO_2Et$ may be converted to compounds of formula (24) using 6N hydrochloric acid at about reflux temperature. The (24) product is isolated by anion or cation exchange chromatography.

The (23) compounds wherein $R_{20}$ is CN may be converted to compounds of formula (24) using $nBu_3SnN_3$ at about 80° C., then 6N hydrochloric acid is added at about reflux temperature. The (24) product is isolated by anion or cation exchange chromatography.

Scheme (VII) illustrates one possible stereochemical configuration. It is understood that reactants having different configurations will produce the corresponding diastereomeric product.

Certain classes of the compounds described by the formulas above are preferred for use in the process of this invention, and certain conditions of operating the process are preferred conditions. The listing below illustrates the preferred conditions and intermediates in tabular form. It will be understood that various preferred conditions and intermediates may be combined to create different, more limited preferred modes of the invention.

a) $R_1$ is

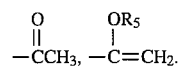

b) $R_3$ is $CH_3$, benzyl, or substituted benzyl.

c) $R_{11}$ is $CO_2R_2$; $R_2$ is $C_1$–$C_6$ alkyl or $C_7$–$C_{10}$ arylalkyl.

d) X is

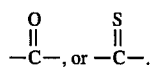

e) $R_5$ is silyl.
f) $R_4$ is hydrogen.
g) Q is

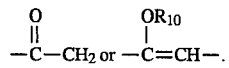

h) $R_{10}$ is silyl.
i) The silyl compound is $(C_1-C_4 \text{ alkyl})Si(R_{14})_2$ Y, $(C_1-C_4 \text{ alkyl})_2Si(R_{14})$ Y, and $Si(R_{14})_3$ Y; wherein $R_{14}$ is independently selected from the group consisting of $C_1-C_4$ alkyl, and aryl; wherein Y is halide or triflate.
j) The tertiary amine base is

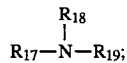

wherein $R_{17}$, $R_{18}$, and $R_{19}$ are independently selected from the group consisting of $C_1-C_8$ alkyl; wherein $R_{17}$ and $R_{18}$ together may form a five to eight member saturated heterocyclic ring with the nitrogen; wherein $R_{17}$ and $R_{18}$ together may form a five to eight member unsaturated heterocyclic ring with the nitrogen.
k) The organic solvent is selected from the group consisting of halogenated hydrocarbons, ether, toluene, xylene, and tetrahydrofuran.
l) The organic solvent is a halogenated hydrocarbon.
m) The tertiary amine base is selected from the group consisting of triethylamine, diisopropylethylamine, pyridine, 2,4,6-trimethylpyridine, 2,6-dimethylpryridine, 2,6-di-t-butylpyridine, 2,6-di-t-butyl-4-methylpyridine, 4-pyrrolidinopyridine, 4-dimethylaminopyridine, and N-methylmorpholine.
n) The silyl compound is a silyl triflate.
o) The organic solvent is tetrahydrofuran or dichloromethane.
p) The silyl compound is trimethylsilyl triflate, triethylsilyl triflate, or tert-butyldimethylsilyl triflate.
q) $R_3$ is benzyl.
r) $R_{11}$ is $CO_2R_2$; $R_2$ is $C_1-C_6$ alkyl.
s) $R_4$ is hydrogen.
t) X is

u) $R_1$ is

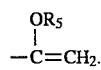

v) $R_5$ is a silyl selected from the group consisting of $Si(R_{14})_3$, $(C_1-C_6 \text{ alkyl})Si(R_{14})_2$, $(C_1-C_6 \text{ alkyl})_2Si(R_{14})$; wherein $R_{14}$ is independently selected from the group consisting of $C_1-C_6$ alkyl and aryl.
w) $R_{10}$ is a silyl selected from the group consisting of $Si(R_{14})_3$, $(C_1-C_6 \text{ alkyl})Si(R_{14})_2$, $(C_1-C_6 \text{ alkyl})_2Si(R_{14})$;

wherein $R_{14}$ is independently selected from the group consisting of $C_1-C_6$ alkyl and aryl.
x) $R_3$ is $CH_3$, benzyl, $COR_6$, $CON(R_6)_2$, $SO_2R_6$, or substituted benzyl.
y) $R_4$ is hydrogen or $SO_2R_2$.

The preferred intermediates of this invention for use in the process of this invention include the features of a–h. The preferred process of this invention uses the conditions of i–k.

The more preferred conditions and intermediates of this invention include the features of a–h, and l–n. The most preferred conditions and intermediates of this invention include the features of m, and o–w.

When compounds wherein X is $CH_2$ are desired, the preferred conditions and intermediates of this invention for use in the process of this invention include the features of a, c, e, g, h, x, and y. When X is $CH_2$ the more preferred conditions and intermediates include the features of l–n, q, r, and u–y.

PREPARATION 1

Preparation of Methyl 2S-N-carbobenzoxy-2-amino-4-oxobutanoate

N-Carbobenzoxy-L-aspartic acid α-methyl ester (40 g) was stirred with thionyl chloride (100 mL) under nitrogen overnight at room temperature, then concentrated in vacuo to dryness. To this acid chloride was added tetrahydrofuran (400 mL), tetrakis(triphenylphosphine)palladium (0) (7 g), and tri-n-butyltin hydride (42 mL). The mixture was stirred for about 4 hours and more tetrakis(triphenylphosphine)palladium (0) (5 g) was added. One hour later more tri-n-butyltin hydride (30 mL) was added. After another 15 minutes $^1$H NMR analysis indicated that the reaction was complete. The reaction was concentrated in vacuo, the residue dissolved in ether (1000 mL), the precipitate removed by filtration and the filtrate concentrated in vacuo. The residue was dissolved in ether (500 mL), the precipitate removed by filtration and the filtrate concentrated in vacuo. The residue was dissolved in acetonitrile (500 mL), washed three times with pentane (300 mL), then the acetonitrile layer was concentrated in vacuo to afford 35 g of the title compound as a brown oil.

PREPARATION 2

Preparation of Methyl 2S-N-carbobenzoxy-2-amino-4,4-dimethoxybutanoate

A mixture of methyl 2S-N-carbobenzoxy-2-amino-4-oxobutanoate (30 g), methanol (300 mL), trimethyl orthoformate (16.6 mL), and p-toluenesufonic acid (2.5 g) was heated to reflux for 30 minutes. The mixture was cooled to room temperature, concentrated in vacuo, and partitioned between saturated aqueous sodium bicarbonate (100 mL) and dichloromethane (500 mL). The aqueous phase was separated and extracted twice with dichloromethane (300 mL), and the combined organic extracts were dried over magnesium sulfate, filtered and concentrated in vacuo. Flash chromatogrpahy of the residue with 65% ethyl acetate/hexane afforded 29 g of the title compound.
$^1$H NMR (CDCl$_3$) δ: 2.09 (q, J=6 Hz, 2H), 3.29 (s, 3H), 3.32 (s, 3H), 3.73 (s, 3H), 4.42 (t, J=5 Hz, 2H), 5.10 (s, 2H), 5.66 (d, J=6 Hz, 1H), 7.34 (s, 5H).
Analysis calculated for $C_{15}H_{21}NO_6$: %C, 57.87; %H, 6.80; N, 4.50. Found: %C, 57.89; %H, 6.80; %N, 4.66.
$[\alpha]_D = -26.6°$ (c=1, methanol)

PREPARATION 3

Preparation of Methyl 2S-2-N-benzylamino-4,4-dimethoxybutanoate 20 g of methyl 2S-N-carbobenzoxy-2-amino-4,4-dimethoxybutanoate in methanol (300 mL) was hydrogenated overnight with 5% palladium on carbon (20 g) at room temperature and 40 psi. The mixture was filtered through diatomaceous earth and the filtrate concentrated in vacuo to afford 9.5 g of methyl 2S-2-amino-4,4 -dimethoxybutanoate. A mixture of the above compound (3.7 g), triethylamine (5.3 mL), dimethylformamide (20 mL) and benzyl bromide (2.5 mL) was stirred about 56 hours at room temperature under nitrogen, then concentrated in vacuo. The residue was partitioned between water (10 mL) and dichloromethane (40 mL), the aqueous phase was separated and extracted three times with dichloromethane (40 mL), then the combined organic extracts were washed with brine, dried over magnesium sulfate, filtered and concentrated in vacuo. Flash chromatogrpahy of the residue with 30% ethyl acetate/ hexane afforded 3 g of the title compound.

$^1$H NMR (CDCl$_3$) δ: 1.85 (m, 2H), 1.96 (m, 1H), 3.29 (s, 3H), 3.30 (s, 3H), 3.37 (dd, J=8, 5 Hz, 1H), 3.61 (d, J=13 Hz, 1H), 3.72 (s, 3H), 3.82 (d, J=13 Hz, 1H), 4.58 (dd, J=7, 5 Hz, 1H), 7.28 (m, 5H).

Analysis calculated for C$_{14}$H$_{21}$NO$_4$: %C, 62.90; %H, 7.92; %N, 5.24. Found: %C, 62.69; %H, 7.75; %N, 5.29.

$[α]_D$= −38.4° (c=1.25, methanol)

PREPARATION 4

Preparation of Methyl 2S-2-N-acryloyl-2-N-benzylamino-4-oxobutanoate

A. Triethylamine (3.26 mL) was added during a five minute period to a 0° C. solution of methyl 2S-2-N-benzylamino-4,4-dimethoxybutanoate (2.85 g) in dichloromethane (10 mL) under nitrogen. Acryloyl chloride (1.73 mL) was slowly added to the mixture, which was then stirred for 1 hour at room temperature. Water (10 mL) was added and the mixture was extracted three times with dichloromethane. The combined organic extracts were washed with brine, dried over magnesium sulfate, filtered and concentrated in vacuo. Flash chromatogrpahy of the residue with 40% ethyl acetate/hexane afforded 3 g of methyl 2S-2-N-acryloyl-2-N-benzylamino- 4,4-dimethoxybutanoate.

$^1$H NMR (CDCl$_3$) δ: 2.02 (m, 1H), 2.46 (m, 1H), 3.22 (s, 3H), 3.26 (s, 3H), 3.63 (s, 3H), 4.40 (m, 1H), 4.45 (m, 1H), 4.56 (d, J=18 Hz, 1H), 4.72 (d, J=18 Hz, 1H), 5.69 (m, 1H), 6.46 (m, 2H), 7.31 (m, 5H).

$[α]_D$=−83.5° (c=1, methanol)

Analysis calculated for C$_{17}$H$_{23}$NO$_5$: %C, 63.54; %H, 7.21; %N, 4.36. Found: %C, 63.24; %H, 7.18; %N, 4.33.

B. A solution of the above compound (2.75 g) in acetonitrile (40 mL) and 10% aqueous hydrochloric acid (10 mL) was stirred for 1 hour at room temperature. The mixture was quenched with saturated aqueous sodium bicarbonate (50 mL), and the aqueous layer was extracted three times with dichloromethane (50 mL). The combined organic extracts were washed with brine, dried over magnesium sulfate, filtered and concentrated in vacuo. Flash chromatogrpahy of the residue with 40% ethyl acetate/hexane afforded 2.3 g of the title compound.

$^1$H NMR (CDCl$_3$) δ: 2.80 (dd, J=18, 6 Hz, 1H), 3.60 (dd, J= 18, 6 Hz, 1H), 3.66 (s, 3H), 4.66 (t, J=6 Hz, 1H), 4.7 (s, 2H), 5.73 (dd, J=12, 4 Hz, 1H), 6.50 (m, 1H), 6.46 (dd, J=20, 1 Hz, 1H), 7.20–7.42 (m, 5H), 9.70(s, 1H).

Analysis calculated for C$_{15}$H$_{19}$NO$_4$: %C, 65.44; %H, 6.22; N, 5.09. Found: %C, 65.15; %H, 6.35; %N, 5.00.

$[α]_D$= −96.1° (c=1, methanol)

PREPARATION 5

Preparation of methyl 2S-2-N-acryloyl-2-N-carbobenzoxy-4,4-dimethoxybutanoate

To a solution of methyl 2S-N-carbobenzoxy-2-amino-4,4-dimethoxybutanoate (0.52 g) in tetrahydrofuran (10 mL) under nitrogen at −78° C. was added potassium bis(trimethylsilyl)amide (3.5 mL) dropwise, and the mixture was stirred at −78° C. for 10 minutes. Acryloyl chloride (0.27 mL) was added and the mixture was warmed to 0° C. and stirred for 1 hour. The reaction was quenched with water and then extracted three times with dichloromethane. The combined organic extracts were dried over magnesium sulfate, filtered and concentrated in vacuo to yield 0.08 g of the title compound.

$^1$H NMR (CDCl$_3$) δ: 2.1 (m, 1H), 2.48 (m, 1H), 3.22 ( s, 3H), 3.24 (s, 3H), 3.51 (s, 3H), 4.42 (t, J=6 Hz, 1H), 5.18 (d, J=12 Hz, 1H), 5.24 (d, J=12 Hz, 1H), 5.30–5.40 (m, 1H), 5.79 (d, J=12 Hz, 1H), 6.40 (d, J=20 Hz, 1H), 7.04 (dd, J=20, 12 Hz, 1H), 7.40 (s, 5H).

EXAMPLE 1

Preparation of methyl 2S-2-N-acryloyl-2-N-benzylamino-6-oxo-hept- 4-E-enoate

A mixture of methyl 2S-2-N-acryloyl-2-N-benzylamino-4-oxobutanoate (3.1 g) and 1-(triphenylphosphoranylidene)-2-propanone (4.7 g) in tetrahydrofuran (50 mL) was refluxed overnight under nitrogen. The mixture was concentrated in vacuo, treated with ether (250 mL), the resulting white precipitate of triphenylphosphine oxide was removed by filtration, and the filtrate was concentrated in vacuo. Flash chromatogrpahy of the residue with 30% ethyl acetate/ hexane afforded 3.77 g of the title compound as an inseperable mixture with triphenylphosphine oxide.

$^1$H NMR (CDCl$_3$) δ: 2.15 (s, 3H), 2.73 (m, 1H), 2.92 (m, 1H), 3.65 (s, 3H), 4.61 (m, 3H), 5.74 (dd, J=10, 3 Hz, 1H), 5.94 (d, J=16 Hz, 1H), 6.46 (m, 2H), 6.59 (dt, J= 16, 10 Hz, 1H), 7.26 (m, 5H).

EXAMPLE 1a

Preparation of methyl 2S-2-N-acryloyl-2-N-benzylamino-6-oxo-hept- 4-E-enoate using Horner Emmons reaction To a suspension of sodium hydride (0.94 g, 60% by weight in mineral oil) in tetrahydrofuran (65 mL) was added diethyl (2-oxopropyl)phosphonate (5.3 g) and the mixture was stirred at room temperature under nitrogen. Within several minutes a colorless homogeneous mixture formed. This mixture was cooled to 0° C., a sample of methyl 2S-2-N-acryloyl- 2-N-benzylamino-4-oxobutanoate (5.4 g) in tetrahydrofuran (12 mL) was added dropwise and then stirred for 1.5 hours at 0° C. The mixture was quenched with water and extracted three times with ethyl acetate. The combined organic extracts were dried over magnesium sulfate, filtered and concentrated in vacuo. Flash chromatogrpahy of the residue with 50% ethyl acetate/hexane afforded 4.0 g of the title compound.

$^1$H NMR (CDCl$_3$) δ: 2.15 (s, 3H), 2.73 (m, 1H), 2.92 (m, 1H), 3.65 (s, 3H), 4.61 (m, 3H), 5.74 (dd, J=10, 3 Hz, 1H), 5.94 (d, J=16 Hz, 1H), 6.46 (m, 2H), 6.59 (dt, J= 16, 10 Hz, 1H), 7.26 (m, 5H).

Analysis calculated for C$_{18}$H$_{21}$NO$_4$: %C, 68.55; %H, 6.71; %N, 4.44. Found: %C, 68.35; %H, 6.89; %N, 4.44.

$[α]_D$=−74.8° (c=1, methanol)

EXAMPLE 2

Preparation of methyl 3S,4aS,8aR-N-benzyl-1,6-dioxo- 1,2,3,4,4a,5,6,7,8,8a-decahydroisoquinoline-3-carboxylate using triethylsilyl trifluoromethanesulfonate A solution of triethylsilyl trifluoromethanesulfonate (0.86 mL) and triethylamine (0.66 mL) in deuterodichloromethane-d$_2$ (10 mL) was stirred at room temperature for 5 minutes. To this mixture was then added a solution of methyl 2S-2-N-acryloyl-2-N-benzylamino-6-oxo-hept- 4-E-enoate (1.0 g, prepared using the method of Example 1a) in deuterodichloromethane-d$_2$ (1 mL), and the resulting mixture was stirred 1 hour at room temperature. $^1$H NMR analysis shows cyclization had occured. A portion of saturated aqueous sodium bicarbonate (10 mL) was added to the mixture, the organic phase was separated and the aqueous phase extracted three times with dichloromethane (10 mL). The combined organic extracts were washed with brine, dried over magnesium sulfate, filtered and concentrated in vacuo to give 1.0 g of methyl 3S,4aS,8aR-N-benzyl- 1-oxo-6-(triethylsilyl(oxy))-1,2,3,4,4a,7,8,8a-octahydroisoquinoline- 3-carboxylate.

A mixture of the above compound (1.0 g) and potassium fluoride dihydrate (0.35 g) in methanol (5 mL) was stirred overnight at room temperature, then concentrated in vacuo. The residue was partitioned between water (5 mL) and dichlromethane (10 mL). The organic layer was separated and the aqueous layer extracted twice with dichlromethane (10 mL). The combined organic extracts were washed with brine, dried over magnesium sulfate, filtered and concetrated in vacuo to afford 0.6 g of a solid. Recrystalliztion from ethyl acetate afforded 0.4 g of the title compound.

Gas chromatographic analysis of the crude title compound prior to recrystallization on an HP5890 Series II capillary GC with an Ultra 1 crosslinked methyl silicone column, 25 m×0.32 mm×0.52 µm, at a column temperature of 240° C., showed three major products, with retention times of 10.14, 11.15 and 11.33 minutes, in a ratio of 70.6%:14.6%:14.8%, respectively. Gas chromatographic analysis of the title compound after recrystallization on an HP5890 Series II capillary GC with an Ultra 1 crosslinked methyl silicone column, 25 m×0.32 mm×0.52 µm, at a column temperature of 240° C., showed a single compound, with retention time of 10.14 minutes.

m.p. 157.8° C.

$^1$H NMR (CDCl$_3$) δ: 1.91–2.15 (m, 4H), 2.24–2.40 (m, 4H), 2.59 (m, 1H), 2.89 (m, 1H), 3.68 (d, J=15 Hz, 1H), 3.72 (s, 3H), 3.95 (q, J=6 Hz, 1H), 5.47 (d, J=13 Hz, 1H), 7.14–7.36 (m, 5H).

Analysis calculated for C$_{18}$H$_{21}$NO$_4$: %C, 68.55; %H, 6.71; %N, 4.44. Found: %C, 68.31; %H, 6.83; %N, 4.40.

[α]$_D$=−24.0° (c=1, methanol).

EXAMPLE 3

Preparation of methyl 3S,4aS,8aR-N-benzyl-1,6-dioxo- 1,2,3,4,4a,5,6,7,8,8a-decahydroisoquinoline-3-carboxylate using tert-butyldimethylsilyl trifluoromethanesulfonate A solution of tert-butyldimethylsilyl trifluoromethanesulfonate (0.1 mL) and triethylamine (0.1 mL) in deuterodichloromethane-d$_2$ (2 mL) was stirred at room temperature for 5 minutes. To this mixture was then added a solution of methyl 2S-2-N-acryloyl-2-N-benzylamino-6-oxo-hept- 4-E-enoate (0.5 g), prepared using the method of Example 1a, in deuterodichloromethane-d$_2$ (0.5 mL), and the resulting mixture was stirred 1.5 hours at room temperature. $^1$H NMR analysis shows enol silyl ether formation, with no cyclization. To the mixture was added silica gel (0.05 g, flash chromatography grade) and stir for 3 days at room temperature. The reaction was filtered, and $^1$H NMR analysis showed cyclization had occured. A portion of saturated aqueous sodium bicarbonate (2 mL) was added to the mixture, the organic phase was separated and the aqueous phase extracted three times with dichloromethane (5 mL). The combined organic extracts were washed with brine, dried over magnesium sulfate, filtered and concentrated in vacuo to give methyl 3S,4aS,8aR-N-benzyl- 1-oxo-6-(t-butyldimethylsilyl(oxy))- 1,2,3,4,4a,7,8,8a-octahydroisoquinoline-3-carboxylate.

A mixture of the above compound and potassium fluoride dihydrate (0.05 g) in methanol (5 mL) was refluxed for 2 hours, then cooled and concentrated in vacuo. The residue was partitioned between water (10 mL) and ethyl acetate (50 mL), the aqueous phase was separated and extracted three times with ethyl acetate (50 mL), then the combined organic extracts were washed with brine, dried over magnesium sulfate, filtered and concentrated in vacuo to afford the crude title compound.

Gas chromatographic analysis of the crude title compound prior to recrystallization on an HP5890 Series II capillary GC with an Ultra 1 crosslinked methyl silicone column, 25 m×0.32 mm×0.52 µm, at a column temperature of 240° C., showed three major products, with retention times of 10.14, 11.15 and 11.33 minutes, in a ratio of 68.3%:18.0%:13.7%, respectively.

EXAMPLE 4

Preparation of methyl 3S,4aS,8aR-N-benzyl-1,6-dioxo- 1,2,3,4,4a,5,6,7,8,8a-decahydroisoquinoline-3-carboxylate using trimethylsilyltriflate A solution of trimethylsilyl trifluoromethanesulfonate (0.11 mL) and triethylamine (0.1 mL) in deuterodichloromethane-d$_2$ (2 mL) was stirred at room temperature for 5 minutes. To this mixture was then added a solution of methyl 2S-2-N-acryloyl-2-N-benzylamino-6-oxo- hept-4-E-enoate (0.5 g), prepared using the method of Example 1a, in deuterodichloromethane-d$_2$ (0.5 mL), and the resulting mixture was stirred for 3 days at room temperature. $^1$H NMR analysis showed cyclization had occured. A portion of saturated aqueous sodium bicarbonate (2 mL) was added to the mixture, the organic phase was separated and the aqueous phase extracted three times with dichloromethane (5 mL). The combined organic extracts were washed with brine, dried over magnesium sulfate, filtered and concentrated in vacuo to give methyl 3S,4aS,8aR-N-benzyl-1-oxo- 6-(trimethylsilyl(oxy))- 1,2,3,4,4a,7,8,8a-octahydroisoquinoline-3-carboxylate.

A mixture of the above compound and potassium fluoride dihydrate (0.05 g) in methanol (5 mL) was refluxed for 2 hours, then cooled and concentrated in vacuo. The residue was partitioned between water (10 mL) and ethyl acetate (50 mL), the aqueous phase was separated and extracted three times with ethyl acetate (50 mL), then the combined organic extracts were washed with brine, dried over magnesium sulfate, filtered and concentrated in wacuo to afford the crude title compound.

Gas chromatographic analysis of the crude title compound prior to recrystallization on an HP5890 Series II capillary GC with an Ultra 1 crosslinked methyl silicone column, 25 m×0.32 mm×0.52 µm, at a column temperature of 240° C., showed three major products, with retention times of 10.14, 11.15 and 11.33 minutes, in a ratio of 59.8%:27.9%:12.3%, respectively.

EXAMPLE 5

Preparation of ethyl 3SR,4aSR,8aRS-6-oxo- 1,2,3,4,4a,5,6,7,8,8a-decahydroisoquinoline-3-carboxylate A mixture of iodotrimethylsilane (7.1 g) and ethyl 3SR, 4aSR,8aRS-6-oxo-N-carbomethoxy-1,2,3,4,4a,5,6,7,8,8a-decahydroisoquinoline- 3-carboxylate (5 g) in chloroform (25 mL) was refluxed for 2.5 hours, then quenched with saturated aqueous sodium bicarbonate and extracted three times with dichloromethane. The combined organic extracts were washed with brine, dried over magnesium sulfate, filtered and concentrated in vacuo to yield 2.3 g of the title compound.

EXAMPLE 6

Preparation of ethyl 3SR,4aSR,8aRS-6-oxo-N-benzyl- 1,2,3,4,4a,5,6,7,8,8a-decahydroisoquinoline-3-carboxylate A mixture of ethyl 3SR,4aSR,8aRS-6-oxo- 1,2,3,4,4a,5,6,7,8,8a-decahydroisoquinoline-3-carboxylate (2.3 g), diisopropylethylamine (1.0 g) and benzyl bromide (2.2 g) in dimethylformamide (10 mL) was heated to 40° C. under nitrogen overnight. The mixture was cooled and concentrated in vacuo, then partitioned between saturated aqueous sodium bicarbonate and dichloromethane. The organic layer was separated and the aqueous layer extracted twice with dichloromethane. The combined organic extracts were washed with brine, dried over magnesium sulfate, filtered and concentrated in vacuo. The residue was filtered through a small plug of silica gel to afford 2 g of the title compound.

EXAMPLE 7

Preparation of 3SR,4aSR,8aRS-6-oxo-N-benzyl- 1,2,3,4,4a,5,6,7,8,8a-decahydroisoquinoline-3-carboxylic acid A mixture of ethyl 3SR,4aSR,8aRS-6-oxo-N-benzyl- 1,2,3,4,4a,5,6,7,8,8a-decahydroisoquinoline-3-carboxylate (0.33 g) and 1N sodium hydroxide (1.2 mL) in ethanol (5 mL) was heated to 80° C. for 48 hours. At this time, an additional aliquot of 1N sodium hydroxide (1.19 mL) was added and the mixture was stirred for another 72 hours at 80° C. The mixture was cooled and concentrated in vacuo to yield 0.30 g of the title compound.

EXAMPLE 8

Preparation of methyl 3SR,4aSR,8aRS-6-oxo-N-benzyl-1,2,3,4,4a,5,6,7,8,8a-decahydroisoquinoline-3-carboxylate A mixture of 3SR,4aSR,8aRS-6-oxo-N-benzyl- 1,2,3,4,4a,5,6,7,8,8a-decahydroisoquinoline-3-carboxylic acid (0.30 g) was refluxed overnight in methanol saturated with hydrochloric acid. The mixture was cooled, and concentrated in vacuo to yield a brown oil. The residue was partitioned between saturated aqueous sodium bicarbonate and dichloromethane. The organic layer was separated and the aqueous layer extracted twice with dichloromethane. The combined organic extracts were washed with brine, dried over magnesium sulfate, filtered and concentrated in vacuo to afford the title compound.

Chiral pack HPLC analysis on a Chiracel® OJ column, 4.6×250 mm, eluting with 4% ethanol/hexane, at a flow rate of 2.5 mL/min, with UV detection at 220 nm, shows two equal peaks with retention times of 7.66 and 9.00 minutes. The compound of Example 8 may be used as a reference to establish enantiomeric purity for the product of example 11A.

EXAMPLE 9

Preparation of methyl 3SR,4aSR,8aRS-N-carbomethoxy-6-oxo- 1,2,3,4,4a,5,6,7,8,8a-decahydroisoquinoline-3-carboxylate To a room temperature solution of magnesium (4.3 g) in methanol (250 mL) was added ethyl 3SR,4aSR,8aRS-N-carbomethoxy- 6-oxo-1,2,3,4,4a,5,6,7,8-decahydroisoquinoline- 3-carboxylate (5.0 g). The mixture was stirred 3 days at room temperature then concentrated in vacuo. The residue was partitioned between 6N hydrochloric acid (50 mL) and ethyl acetate (100 mL), the organic phase separated and the aqueous phase extracted twice with ethyl acetate (100 mL). The combined organic extracts were dried over magnesium sulfate, filtered and concentrated in vacuo. Flash chromatography of the residue with 50% ethyl acetate/hexane afforded 3.5 g of the title compound.

Gas chromatographic analysis on an HP5890 Series II capillary GC with an Ultra 1 crosslinked methyl silicone column, 25 m×0.32 mm×0.52 μm, at a column temperature of 240° C., showed a retention time of 2.47 min, 97.7% diasteromerically pure.

$^1$H NMR (CDCl$_3$, doubling due to amide rotamers) δ: 1.60– 2.40 (m, 9H), 2.59 (dd, J=14, 6 Hz, 1H), 3.30 and 3.20 (dd, J=14, 3 Hz, 1H), 3.71 and 3.68 (s, 3H), 3.73 (s, 3H), 4.06 and 3.91 (d, J=14 Hz, 1H), 4.99 and 4.91 (d, J= 6 Hz, 1H).

Analysis calculated for C$_{13}$H$_{19}$NO$_5$: %C, 57.98; %H, 7.11; %N, 5.20. Found: %C, 58.13; %H, 7.11; %N, 5.13.

EXAMPLE 10

Preparation of methyl 3S,4aS,8aR-N-benzyl-1-oxo-6,6-dimethoxy- 1,2,3,4,4a,5,6,7,8,8a-decahydroisoquinoline-3-carboxylate A mixture of methyl 3S,4aS,8aR-N-benzyl-1,6-dioxo-1,2,3,4,4a,5,6,7,8,8a-decahydroisoquinoline-3-carboxylate (0.25 g), p-toluene sulfonic acid (0,030 g) and trimethylorthoformate (0.11 g) in methanol (10 mL) was refluxed under nitrogen for 1.5 hours, then cooled and partitioned between saturated aqueous sodium bicarbonate and dichloromethane. The organic layer was separated and the aqueous layer extracted twice with dichloromethane. The combined organic extracts were washed with brine, dried over magnesium sulfate, filtered and concentrated in vacuo to afford 0.32 g of the title compound.

EXAMPLE 11

Preparation of methyl 3S,4aS,8aR-N-carbomethoxy-6-oxo-1,2,3,4,4a,5,6,7,8,8a-decahydroisoquinoline-3-carboxylate A. A mixture of methyl 3S,4aS,8aR-N-benzyl-1-oxo-6,6-dimethoxy- 1,2,3,4,4a,5,6,7,8,8a-decahydroisoquinoline-3-carboxylate (0.32 g) and borane-methyl sulfide (0.53 mL of a 2.0M solution in tetrahydrofuran) in tetrahydrofuran (5 mL), was refluxed for 3 hours. To this solution was added 6N hydrochloric acid (1 mL) and the reflux was continued for an additional 30 minutes. The mixture was cooled, quenched with saturated aqueous sodium bicarbonate, and extracted three times with ethyl acetate. The combined organic extracts were washed with brine, dried over magnesium sulfate, filtered and concentrated in vacuo. Radial chromatography with 30% ethyl acetate/hexane afforded 0.07 g of methyl 3S,4aS,8aR-N-benzyl-6-oxo- 1,2,3,4,4a,5,6,7,8,8a-decahydroisoquinoline-3-carboxylate. Chiral pack HPLC analysis on a Chiracel® OJ column, 4.6× 250 mm, eluting with 4% ethanol/hexane, at a flow rate of 2.5 mL/min, with UV detection at 220 nm, shows only one peak with a retention time of 7.62 minutes, >99% enantiomerically pure. m.p. 115.3° C.

$^1$H NMR (CDCl$_3$) δ: 1.70–1.86 (m, 4H), 2.08–2.54 (m, 7H), 3.23 (dd, J=12, 2 Hz, 1H), 3.51 (t, J=4 Hz, 1H), 3.71 (s, 4H), 7.21–7.29 (m, 5H).

FD mass spectra: m/e=301.
$[\alpha]_D = -46.0°$ (c=1, methanol).

B. A mixture of methyl 3S,4aS,8aR-N-benzyl-6-oxo-1,2,3,4,4a,5,6,7,8,8a-decahydroisoquinoline-3-carboxylate (0.15 g, >99% enantiomerically pure), methylchloroformate (1.6 mL) and methanol (10 mL) was refluxed overnight. An additional aliquot of methylchloroformate (1.6 mL) was added and the mixture was refluxed until the reaction was complete. The mixture was concentrated in vacuo to yield 0.13 g of the title compound. Flash chromatography of the residue with 50% ethyl acetate/hexane afforded 0.035 g of the title compound, whose $^1$H NMR spectrum was identical to that of the racemic compound prepared in example 9.

Gas chromatographic analysis on an HP5890 Series II capillary GC with an Ultra 1 crosslinked methyl silicone column, 25 m×0.32 mm×0.52 μm, at a column temperature of 240° C., showed a retention time of 2.47 min, 96.5% diastereomerically pure. This retention time is identical with the racemic compound from example 9.

m.p. 114.5° C.

Analysis calculated for $C_{13}H_{19}NO_5$: %C, 57.98; %H, 7.11; N, 5.20. Found: %C, 57.87; %H, 7.27; %N, 5.19.

$[\alpha]_D = -55.0°$ (c=1, methanol)

We claim:

1. An enantioselective process for preparing a compound of formula (IIa)

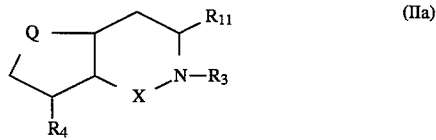

wherein $R_{11}$ is $CO_2R_2$, $CON(R_2)_2$, CN, $CH_2OH$, or protected hydroxymethyl;

$R_2$ is independently hydrogen, $C_1$–$C_6$ alkyl, $C_3$–$C_6$ alkenyl, aryl, or $C_7$–$C_{16}$ arylalkyl;

$R_3$ is hydrogen, $C_1$–$C_6$ alkyl, $C_3$–$C_6$ alkenyl, $CON(R_6)_2$, $SO_2R_6$, $COR_6$, $CO_2R_6$, benzyl, or substituted benzyl having from one to two substituents independently selected from the group consisting of $C_1$–$C_6$ alkyl, $C_3$–$C_8$ cycloalkyl, $NO_2$, halo, halo($C_1$–$C_6$)alkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl;

$R_4$ is hydrogen or CHO;

X is —$CH_2$—,

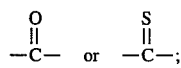

$R_6$ and $R_7$ independently are selected from the group consisting of $C_1$–$C_6$ alkyl, aryl, $C_7$–$C_{16}$ arylalkyl, and $C_3$–$C_6$ alkenyl;

Q is

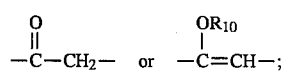

and $R_{10}$ is silyl, $C_1$–$C_4$ alkyl, or $C_1$–$C_{10}$ alkanyoyl;

or a pharmaceutically acceptable salt thereof;

which process comprises contacting a substrate of the formula (Ia)

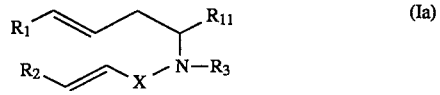

wherein $R_1$ is

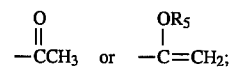

$R_{11}$ is $CO_2R_2$, $CON(R_2)_2$, CN, $CH_2OH$, or protected hydroxymethyl;

$R_2$ is independently hydrogen, $C_1$–$C_6$ alkyl, $C_3$–$C_6$ alkenyl, aryl, and $C_7$–$C_{16}$ arylalkyl;

$R_3$ is hydrogen, $C_1$–$C_6$ alkyl, $C_3$–$C_6$ alkenyl, $CON(R_6)_2$, $SO_2R_6$, $COR_6$, CO2R6, benzyl, or substituted benzyl having from one to two substituents independently selected from the group consisting of $C_1$–$C_6$ alkyl, $C_3$–$C_8$ cycloalkyl, $NO_2$, halo, halo($C_1$–$C_6$)alkyl, $C_3$–$C_6$ alkenyl, $C_3$–$C_8$ cycloalkyl-($C_1$–$C_3$)alkyl, phenyl, $C_5$–$C_8$ cycloalkenyl, $C_5$–$C_8$ cycloalkenyl-($C_1$–$C_3$)alkyl, $COR_2$, $C_1$–$C_{10}$ alkanoyl, $OR_2$, and $C_7$–$C_{16}$ arylalkyl; or X is —$CH_2$—,

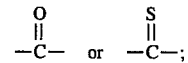

$R_4$ is hydrogen or CHO;

$R_5$ is silyl, $C_1$–$C_4$ alkyl, or $C_1$–$C_{10}$ alkanyoyl; and $R_6$ and $R_7$ independently are selected from the group consisting of $C_1$–$C_6$ alkyl, aryl, $C_7$–$C_{16}$ arylalkyl, and $C_3$–$C_6$ alkenyl;

or a pharmaceutically acceptable salt thereof;

with a silyl compound and a tertiary amine in the presence of an organic solvent.

2. A process of claim 1 wherein the silyl compound is selected from the group consisting of $(C_1$–$C_6$ alkyl)Si$(R_{14})_2$ Y, $(C_1$–$C_6$ alkyl)$_2$Si$(R_{14})$ Y, Si$(R_{14})_3$ Y wherein $R_{14}$ is independently selected from the group consisting of $C_1$–$C_6$ alkyl and aryl; and Y is halide or triflate.

3. A process of claim 2 wherein the tertiary amine base is

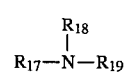

wherein $R_{17}$, $R_{18}$, and $R_{19}$ are independently select from the group consisting of hydrogen, $C_1$–$C_8$ alkyl; wherein $R_{17}$ and $R_{18}$ together with the nitrogen may form a five to eight member saturated or unsaturated heterocyclic ring.

4. A process of claim 3 wherein the organic solvent is selected from the group consisting of halogenated hydrocarbons, ether, toluene, xylene, and tetrahydrofuran.

5. A process of claim 4 wherein the silyl compound is selected from the group consisting of $(C_1$–$C_6$ alkyl)Si$(R_{14})_2$ Y, $(C_1$–$C_6$ alkyl)$_2$Si$(R_{14})$ Y, Si$(R_{14})_3$ Y; and Y is triflate.

6. A process of claim 5 wherein the compound of formula (Ia) is one wherein $R_2$ is $C_1$–$C_6$ alkyl; $R_3$ is benzyl, $CO_2R_7$, or $COR_7$; $R_6$ is $C_1$–$C_6$ alkyl; $R_1$ is

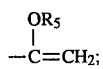

and X is

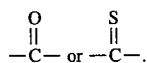

7. A process of claim 5 wherein the silyl compound is selected from the group consisting of trimethylsilyl triflate, triethylsilyl triflate, and tertbutyldimethylsilyl triflate.

8. A process of claim 7 wherein the tertiary amine base is selected from the group consisting of triethylamine, diisopropylethylamine, pyridine, 2,4,6-trimethylpyridine, 2,6-dimethylpryridine, 2,6-di-t-butylpyridine, 2,6-di-t-butyl-4-methylpyridine, 4-pyrrolidinopyridine, 4-dimethylaminopyridine, and N-methylmorpholine.

9. A process of claim 8 wherein the organic solvent is a halogenated hydrocarbon.

10. A process of claim 9 wherein the organic solvent is dichloromethane; the silyl compound is triethylsilyl triflate; and the tertiary amine base is triethylamine.

11. A process of claim 6 wherein the organic solvent is dichloromethane; the silyl compound is triethylsilyl triflate; and the tertiary amine base is triethylamine.

12. A process of claim 11 wherein $R_2$ is methyl and $R_3$ is benzyl.

* * * * *